US006682697B2

(12) United States Patent
He et al.

(10) Patent No.: US 6,682,697 B2
(45) Date of Patent: Jan. 27, 2004

(54) PROCESS FOR STERILIZATION AND DISINFECTING OF AGRICULTURE AND BOTANIC PRODUCTS

(75) Inventors: Kan He, River Edge, NJ (US); Baoliang Cui, Palisade Park, NJ (US); Zhong Guan Shao, Saddle Brook, NJ (US); Natalie I. Koether, Far Hills, NJ (US); Val Madis, Ho Ho Kus, NJ (US); Qun Yi Zheng, Wayne, NJ (US)

(73) Assignee: Pure World Botanicals, Inc., South Hackensack, NJ (US)

( * ) Notice: Subject to any disclaimer, the term of this patent is extended or adjusted under 35 U.S.C. 154(b) by 25 days.

(21) Appl. No.: 10/046,927

(22) Filed: Jan. 15, 2002

(65) Prior Publication Data

US 2003/0194347 A1 Oct. 16, 2003

(51) Int. Cl.⁷ .................................................. A61C 2/00
(52) U.S. Cl. .............................. 422/29; 422/1; 422/21; 422/22; 422/23; 422/24; 422/28; 422/32; 422/34; 426/321; 426/331; 426/335
(58) Field of Search ................................ 422/1, 21, 22, 422/23, 24, 28, 29, 32, 34; 426/321, 331, 335

(56) References Cited

U.S. PATENT DOCUMENTS

| 3,996,386 A | 12/1976 | Malkki et al. .............. 426/321 |
|---|---|---|
| 4,006,265 A | * 2/1977 | Tamas et al. ................ 426/623 |
| 4,512,951 A | 4/1985 | Koubek ........................ 422/33 |
| 4,592,892 A | 6/1986 | Ueno et al. .................... 422/28 |
| 4,863,688 A | 9/1989 | Schmidt et al. ................ 422/28 |
| 5,403,602 A | 4/1995 | Endico ........................ 426/231 |
| 5,405,631 A | 4/1995 | Rosenthal .................... 426/235 |
| 5,460,845 A | * 10/1995 | Dalmasso et al. .......... 426/320 |
| 5,535,667 A | 7/1996 | Dalmasso et al. ............ 99/472 |
| 5,593,714 A | 1/1997 | Hirsch ........................ 426/268 |
| 5,641,530 A | 6/1997 | Chen .......................... 426/532 |
| 5,744,094 A | 4/1998 | Castberg et al. .............. 422/24 |
| 5,817,253 A | 10/1998 | Grimberg et al. ....... 252/186.29 |
| 5,902,619 A | 5/1999 | Rubow et al. ............... 426/235 |
| 5,932,265 A | 8/1999 | Morgan ....................... 426/511 |
| 6,045,846 A | 4/2000 | Bautista et al. ............. 426/335 |
| 6,080,435 A | 6/2000 | Rubow et al. ............... 426/235 |
| 6,086,833 A | 7/2000 | Conners et al. ............. 422/292 |
| 6,150,663 A | 11/2000 | Rosenthal .................... 250/435 |
| 6,162,477 A | 12/2000 | Crisinel et al. .............. 426/256 |
| 6,224,827 B1 | 5/2001 | Lembke ....................... 422/28 |
| 6,245,294 B1 | 6/2001 | Goldberg et al. .............. 422/26 |
| 6,265,006 B1 | 7/2001 | Inglis et al. ................ 426/320 |

OTHER PUBLICATIONS

International Search Report, PCT/US02/39373.

* cited by examiner

Primary Examiner—Krisanne Thornton
(74) Attorney, Agent, or Firm—Steven C. Petersen; Sarah S. O'Rourke; Hogan & Hartson LLP

(57) ABSTRACT

The present invention relates generally to the sterilization and disinfection of agricultural and botanical products such as botanical powders. More particularly, the present invention is directed towards the use of HBS technology whereby contaminated agricultural products are contacted, at ambient pressure, with an oxidant such as nascent oxygen or hydroxyl radicals thus resulting in the oxidization and destruction of the contaminating microorganisms.

29 Claims, 10 Drawing Sheets

PROCESS FOR STERILIZATION AND DISINFECTING OF AGRICULTURE AND BOTANIC PRODUCTS

BACKGROUND OF THE INVENTION

1. Field of the Invention

The present invention relates generally to the sterilization and disinfection of agricultural and botanical products such as botanical powders. More particularly, the present invention is directed towards the use of heterogeneous biphase sterilization (HBS) technology whereby contaminated agricultural products are contacted with an oxidant such as nascent atomic oxygen and/or hydroxyl radicals thus resulting in the oxidization and destruction of the contaminating microorganisms.

2. Description of the State of Art

Herbal powders comprise a large portion of the botanical products sold in the dietary supplement market. These powders are processed by milling raw whole herbs or plants. The resultant powders have a natural profile of chemical constituents unaltered from the plants themselves. However, they also are generally contaminated with the same microbial organisms found on the botanical raw materials which are harvested from farms or are collected from wild fields. Therefore, it is essential to remove the microbial contamination from the herbal powders before they are incorporated into a finished dose form and sold into the market.

Currently, ethylene oxide and gamma irradiation are the dominant modes for sterilizing botanical powders. However, these technologies have been challenged recently due to concerns that gamma irradiation and ethylene oxide residuals found in botanical powders may potentially be harmful to human health. Already Europe and Japan have implemented regulations against the use of one or the other of these technologies.

Other sterilization techniques for botanicals include the application of heat and/or steam. Unfortunately, intense heat and/or steam likely damage the active ingredients in the plants and have proven unreliable in permanently eliminating microbial spores that regenerate after cooling.

Another sterilization technology, ozonization, has recently been mentioned for use with botanical products, but it is uncertain if this technology will be able to permanently eliminate microbes. From a cost point of view, ozonilysis requires significant investment for building a specific facility with property and equipment because ozone has to be generated on site. These facilities are also extremely dangerous due to the highly explosive nature of ozone production.

U.S. Pat. No. 5,460,845, issued Oct. 24, 1995 to Delmassa, et al., shows treating the surface of seeds, nuts, grains, fruits and spices in a dehumidifying chamber, exposing the food to $H_2O_2$ and $H_2O$ vapor under vacuum, followed by removing the peroxide to 38 mm Hg, followed by increasing the pressure to 400–580 mm Hg, for a 3–30 minute exposure. U.S. Pat. No. 5,514,403, issued May 7, 1996 to Webb, et al., teaches killing bacteria on animal carcasses by spraying with superheated steam at 250–300° F. for 1–5 seconds followed immediately by spraying with a cooling liquid for 5–10 seconds. U.S. Pat. No. 5,523,053, issued Jun. 4, 1996 to Daniel H. Dudek, describes sterilizing spices or herbs by dropping the material into pressurized steam sterilization chambers successively for a predetermined period of time, followed by gradual depressurization to atmospheric pressure.

U.S. Pat. No. 5,593,714, issued Jan. 14, 1997 to Gerald P. Hirsch, describes placing a food product in a compressible package at 25,000 psi and 18–23° C. for at least 5 days and optionally adding an anti-oxidant. U.S. Pat. No. 5,641,530, issued Jun. 24, 1997 to T. C. Chen, teaches treating foodstuffs with 0.005% to 0.035% $H_2O_2$ and 0.005 to 0.1% $H_3PO_4$ or $C_6H_5COOH$. U.S. Pat. No. 5,711,981, issued Jan. 27, 1998 to Wilson, et al., describes treating meats by removing surface water by air blowing, steam heating at pressure greater than atmospheric, and chilling by spraying with water.

All of these techniques have suffered from one or more of the following problems: (1) denaturation of protein in food stuff, (2) insufficient bacterial kill, (3) deleterious color change, (4) unacceptable flavor modification, (5) inadequate control of the process in large scale operations, (6) expensive and elaborate process equipment is needed, (7) high atmospheric pressures are required, and (8) difficult to process powdered material with large surface area.

As an example, most of the techniques discussed above require applying a vacuum prior to flushing. This requires the vacuum pump to remove air from an air tight treatment chamber at a prodigious rate, engendering frequent mechanical breakdowns, or slowing the treatment process, which makes the apparatus less economical and less desirable from an industrial perspective. It is an object of the present invention to overcome the difficulties and disadvantages of the prior art.

Because of the multifarious reasons set forth above, existing methods for sterilizing botanical powders are unsatisfactory. The challenge is to develop a competitively priced sterilization process capable of permanently eliminating microbial contamination in botanical powders while maintaining their original chemical and physical properties. These properties include bulk density, flowability, compressibility, mass distribution, moisture content, color, odor and most importantly, chemical composition.

SUMMARY OF THE INVENTION

Accordingly, one object of this invention is to provide a method and apparatus for the sterilization and disinfection of agricultural products.

Another object of this invention is to provide a method of effectively killing microorganisms that exist within botanical powders.

Additional objects, advantages, and novel features of this invention shall be set forth in part in the description and examples that follow, and in part will become apparent to those skilled in the art upon examination of the following or may be learned by the practice of the invention. The objects and the advantages of the invention may be realized and attained by means of the instrumentalities and in combinations particularly pointed out in the appended claims.

To achieve the foregoing and other objects and in accordance with the purposes of the present invention, as embodied and described therein, the process of this invention may comprise contacting at ambient pressure microbial contaminated surfaces with nascent oxygen and/or hydroxyl radicals.

BRIEF DESCRIPTION OF THE DRAWINGS

The accompanying drawings, which are incorporated in and form a part of the specifications, illustrate the preferred embodiments of the present invention, and together with the description serve to explain the principles of the invention.

In the Drawings.

DETAILED DESCRIPTION OF THE PREFERRED EMBODIMENT

Many peroxide compounds, such as hydrogen peroxide ($H_2O_2$), release an oxygen molecule ($O_2$) after their degradation. Before forming the oxygen molecule, atomic oxygen (O) is generated first and this state is called the nascent state. Nascent oxygen or atomic oxygen is characterized by excessive chemical activity that is capable of functioning as a germicide. Since nascent oxygen is a very short acting element, harnessing its germicidal properties for use on specific types of materials is a difficult undertaking. Forming hydroxyl radicals or perhydroxyl radicals from peroxide compounds are also possible if certain reducing or oxidizing agents exist. For example, ferrous ions ($Fe^{2+}$) catalytically convert hydrogen peroxide into hydroxyl radical and ferric ions ($Fe^{3+}$) convert $H_2O_2$ into perhydroxyl radical.

The source of energy may be but is not limited to heat, irradiation (UV), or an enzyme. In general, the process of the present invention exploits the germicidal properties of nascent oxygen, but does not exclude the possibilities of hydroxyl and perhydroxyl radicals, by creating an environment at ambient pressures wherein nascent oxygen is produced and immediately contacted with a surface having microbial contamination whereupon the microbial contaminate is oxidized and thus killed. According to the method of the present invention, any good such as, but not limited to spice, gum, dried vegetable, botanical products in the form of powders, roots, husks, fruits, flowers, barks, leaves, flowers and seeds, or any instrument (organic or inorganic) having a surface capable of being contaminated with microbial organisms, is placed in an environment that is not deleterious to the chemical constituents of the goods or the instrument. Accordingly, once the botanical powder has been exposed to this, "environmental friendly process" the botanical powder is exposed to a nascent oxygen source and a source of energy that will cause the nascent oxygen to be released.

Figure 1:
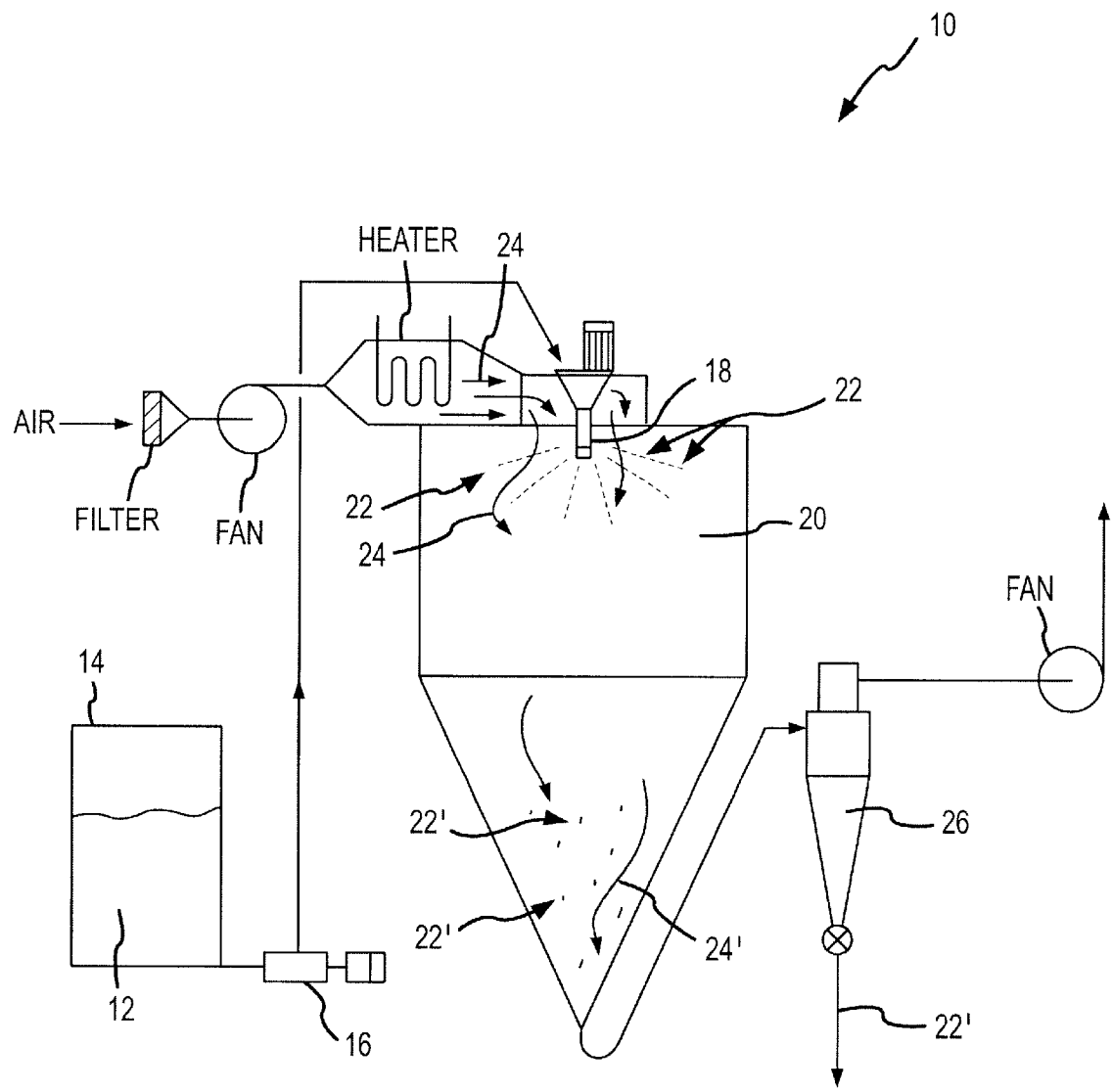
FIG. 1 is a schematic diagram illustrating the Heterogeneous Biphase Sterilization (HBS) process of this invention as applied to a spray drying system.

The Heterogeneous Biphase Sterilization (HBS) process 10 of the present invention is shown in FIG. 1. Referring now to FIG. 1, there is shown in schematic diagram, a mixing and sterilization operation utilizing the HBS process of this invention. The initial stage of the process involves the formulation of feed 12 of agricultural or botanical products such as botanical powders with a source of nascent oxygen and/or hydroxyl radicals which may include hydrogen peroxide (H2O2), however other sources of nascent oxygen such as but not limited to peroxyacetic acid, percarbonates, such as sodium percarbonate may be used. Hydrogen peroxide is the preferred source of nascent oxygen and hydroxyl radicals. Nascent oxygen and hydroxyl radicals are two of the most reactive chemical species, weaker only to the element fluorine, but stronger than ozone, perhydroxyl radical, permangnate, hypobromous acid, chlorine dioxide, chlorine, etc. in their oxidation potential. Hydrogen peroxide is also advantageous since it also produces hydroxyl radicals that also act as oxidants thus further assisting in the oxidation and elimination of microorganisms. Hydrogen peroxide is a natural metabolite of many organisms and it is also formed by the action of sunlight on water—a natural purification system for our environment. Hydrogen peroxide is very unstable and is easily decomposed in air, by increasing temperature, or by reducing agents, to form oxygen and water. Its half-life in fresh water ranges from 8 hours to 20 days and in air from 10 to 20 hours. The half-life of hydrogen peroxide in the environment of botanical powders could be even less with the existence of all kind of reducing sources such as microbes, trace minerals and plants themselves. Thus, the use of hydrogen peroxide is predicted as safe, effective, economical and environmentally friendly.

Feed 12 is formed by mixing a known quantity of botanical powder with hydrogen peroxide in the range of 1%–10% ($H_2O_2$ weight to botanical weight) and water in the range of 10%–60% (botanical weight to total weight). Thus for example, if 1000 kg of botanical powder is used as the starting material, 100 kg of 35% hydrogen peroxide solution may be mixed in to achieve a 3.2% $H_2O_2$ level and 2700 kg water may be added to achieve about 26% of solid in solution.

Feed 12 may be mixed at room temperature or may be mixed at heated conditions up to 50–60° C. It is important to note that while heating feed 12 at higher temperature may in fact degrade the hydrogen peroxide and thereby produce nascent oxygen resulting in reduced microbes, the excessive heat will also damage or "cook" the chemical constituents of the botanical powder, thus destroying the desired product. Furthermore, while given enough time the hydrogen peroxide will naturally degrade and thus produce nascent oxygen it is important that feed 12 be processed upon formation otherwise the aqueous solution may actually start to extract the chemical constituents from the botanical powder thus also destroying the product that is to be decontaminated. The surprising discovery of the present invention was that hydrogen peroxide alone is not sufficient to kill microorganisms, but that the hydrogen peroxide had to be degraded at certain conditions as described in this process to release nascent atomic oxygen and hydrogen radicals which killed the microorganisms efficiently.

Upon the formation of feed 12, pump 16 directs feed 12 through nozzle 18 and into drying chamber 20. Feed 12 is brought to the required pressure by virtue of pump 16 and is subsequently atomized into particles 22 through nozzle 18. Nozzle 18 may be a one component nozzle, a two component nozzle or it may be a centrifugal atomization system. Drying chamber 20 simultaneously also receives heated drying air 24. Heated drying air 24 is introduced into drying chamber 20 at a temperature in the range of 200° F.–500° F. and preferably about 250–450° F. The temperature of drying air 24 will result in the release of nascent oxygen which subsequently contacts the surface of particles 22 thereby oxidizing and destroying contaminating microorganisms residing thereon. In the event that hydrogen peroxide is used as the source for nascent oxygen, hydroxyl radicals will also be produced and these radicals will further destroy contaminating microorganisms. Decontaminated or sterilized particles 22' drop to the bottom of drying chamber 20 and exit drying chamber 20 together with the outgoing air 24' which is now significantly less than 400° F. The particles 22 drop through drying chamber 20 so rapidly that the temperature of drying air 24 has no significant effect on the chemical constituents making up particle 22. However, the brief exposure to drying air 24 is adequate to degrade the hydrogen peroxide that is present and thereby produce nascent atomic oxygen.

In a typical spray drying plant, upon exiting the drying chamber 20 decontaminated particles 22' and outgoing air 24' will be received by cyclone 26. A ventilator (not shown) removes the outgoing air 24', which in many cases is also passed through a filter and a scrubber, while sterilized particles 22' exit through the bottom of cyclone 26 where they are gathered and stored (not shown) for further processing or packaging. Drying chamber 20 illustrated above is a standard unidirectional spray dryer, however it is contemplated that with appropriate modifications one skilled in the art would be able to identify the necessary parameters to successfully utilize a counter-current or mixed-flow (not shown) spray dryer.

Specific apparatus and machinery and variations thereof useful in the present invention are described in the literature, one example of such a text is entitled "Phytopharmaceutical Technology" by P. H. List and P. C. Schmidt, CRC Press (1989) (ISBN 0-8493-7709-0), which is incorporated herein by reference.

Figure 2:
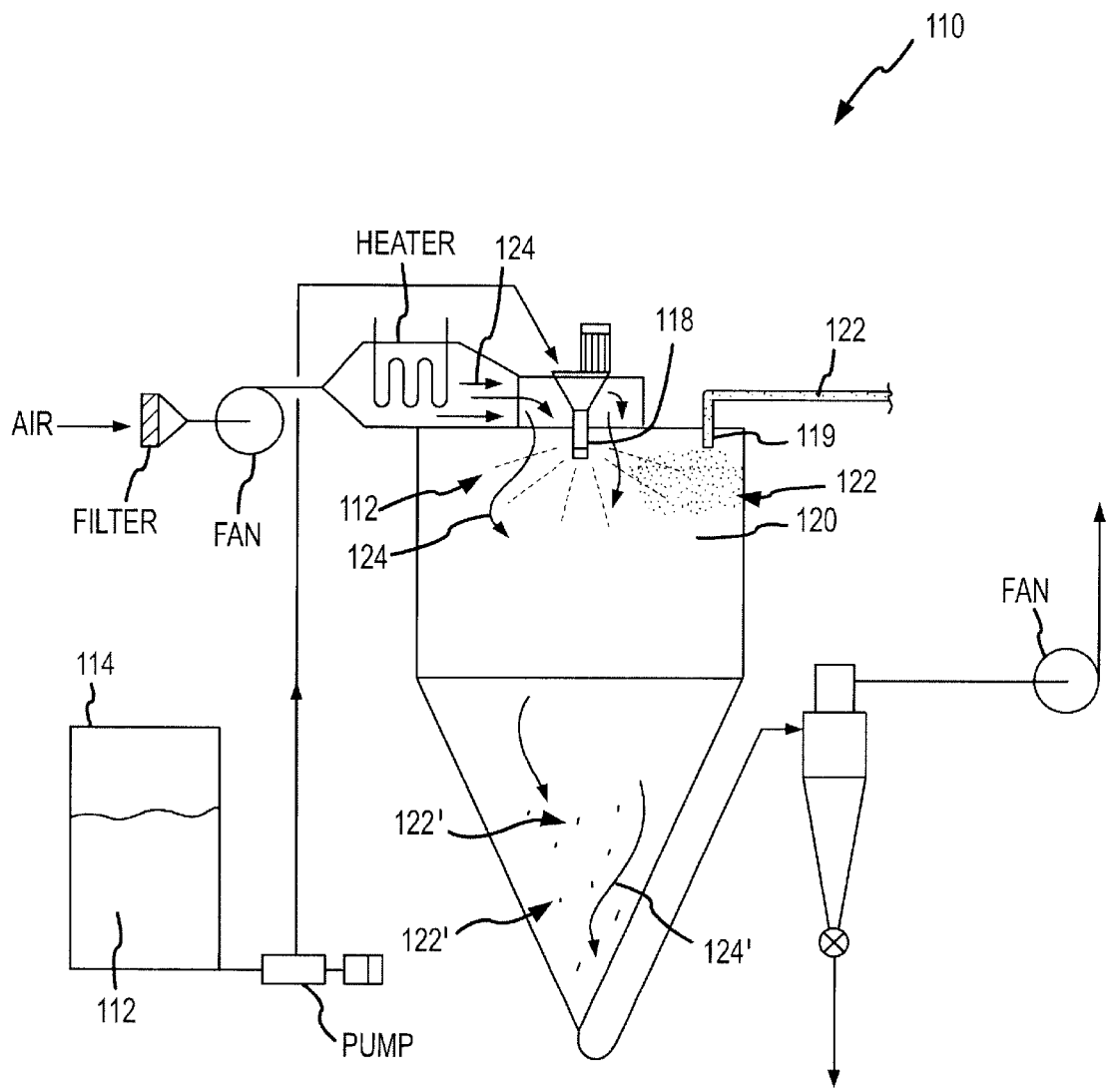
FIG. 2 is a schematic diagram illustrating an alternative embodiment of the HBS process of this invention as applied to a spray drying system.

The above embodiment, shown in FIG. 1, may be modified as shown in FIG. 2. In this particular embodiment 110, drying chamber 120 is brought up to its operational temperature by introducing hot drying air 124. Once the drying chamber 120 is at its operational temperature in the range of 200° F.–500° F. botanical powder 122 and a source of nascent atomic oxygen are simultaneously introduced into drying chamber 120. Botanical powder 122 (contaminated with microorganisms) is stored in a separate vessel (not shown) and pumped directly into the drying chamber 120 through nozzle 119 in a powder form. The source of nascent atomic oxygen, such as but not limited to hydrogen peroxide 112, stored in vessel 114, is also pumped directly into drying chamber 120 through nozzle 118. The source of nascent atomic oxygen is decomposed upon entry into drying chamber 120 and nascent atomic oxygen is released. In the event hydrogen peroxide is the source of nascent atomic oxygen, hydroxyl radicals will also be released. The nascent atomic oxygen (and hydroxyl radicals) will then come in contact with the contaminated botanical powder 122 and oxidize the microorganisms, resulting in a sterile botanical powder 122'.

Figure 3:
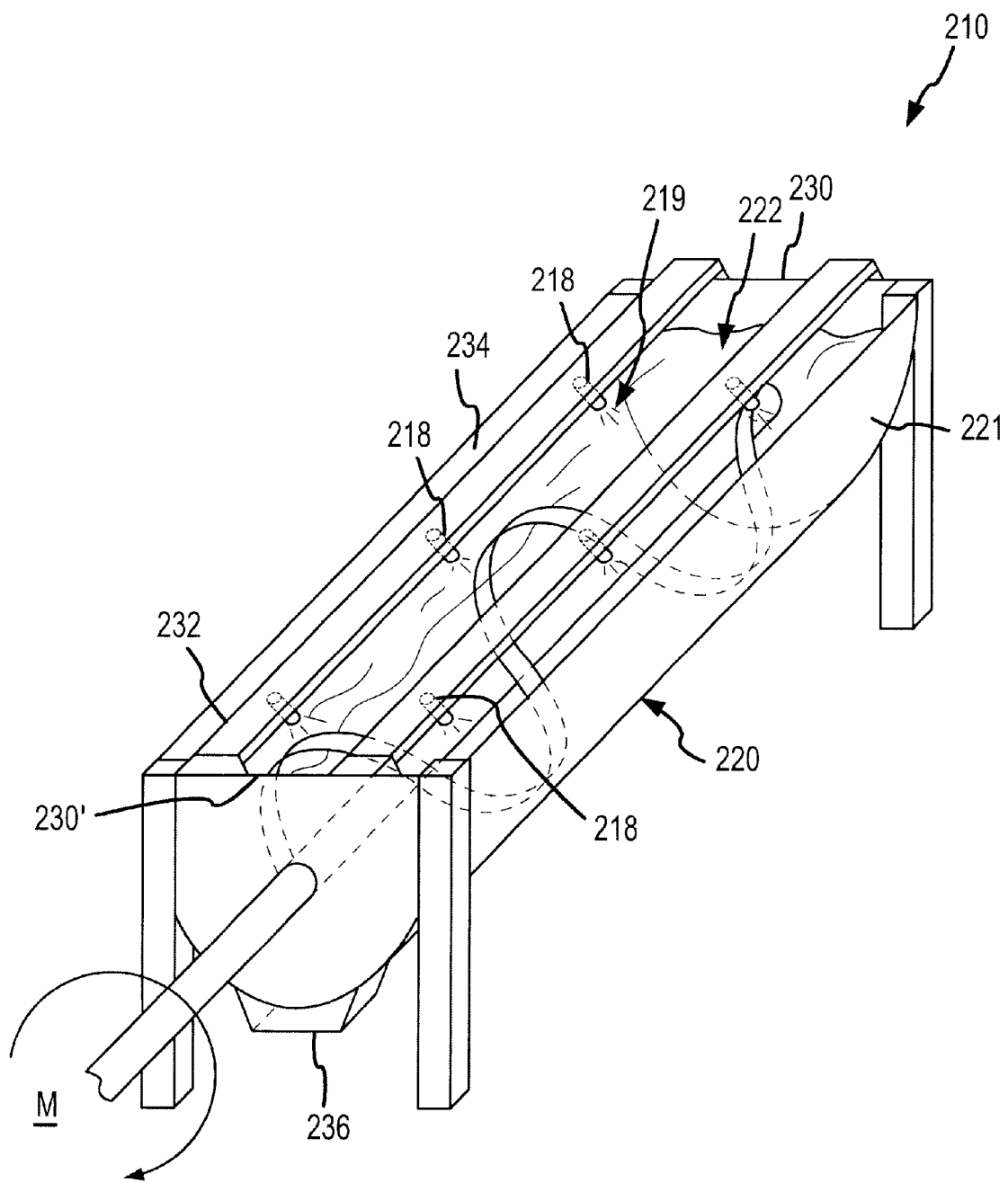
FIG. 3 is a perspective view illustrating the HBS process of this invention as applied to a modified ribbon blender system.

In another embodiment, shown in FIG. 3, the HBS process 210 of the present invention may be accomplished by placing the contaminated botanical powder 222 within a modified stainless steel vessel 220 such as a ribbon blender. The modification made to the ribbon blender is the addition of a pair of manifolds with spray nozzles. This modification allows the hydrogen peroxide solution to be distributed in the blender uniformly throughout the process. The additional modification made to the ribbon blender is the addition of a heating jacket (not shown) placed adjacent to the entire outside surface 221 of the vessel 220. Alternatively, a vessel having hollow sidewalls could be constructed so that water or any other thermally conducting fluid, such as but not limited to oils, and alcohols, could flow through the sidewalls in a completely contained manner and the temperature of the water could easily be varied.

Attached to the upper ends 230 and 230' of vessel 220 is at least one brace 232 which traverses the length of vessel 220 and supports the mounting of nozzles 218. In the alternative, brace 232 could be mounted across the width of vessel 220. The processing sequence according to the present embodiment thus allows for the ribbon blender 220 to mix and heat the botanical powder 222. The internal sidewall 232 of vessel 220 is maintained at a temperature in the range of 40° C.-100° C. and preferably maintained at 50° C.–80° C. As discussed previously, a source of nascent oxygen 219, such as but not limited to hydrogen peroxide solution, is directed through nozzles 218 thus allowing the source of nascent oxygen 219 to come in contact with the heated botanical powder 222. As the mixing continues the source of nascent oxygen 219 is mixed into the botanical powder and as the source of nascent oxygen 219 comes in contact with the internal sidewall 234 the existing heat results in the release of nascent oxygen. As the nascent oxygen is released it oxidizes and destroys the existing contaminating microorganisms that it comes into contact with. Mixing continues for a period of 5 minutes to 180 minutes depending upon the volume of botanical powder 222. In the batch-feed operation as illustrated in FIG. 3, an outfeed door 236 is closed until the botanical powder is thoroughly mixed and the decontamination and sterilization has been completed.

At the completion of the mixing sequence, the sterilized botanical powder 222' is cooled down by flowing cold water through the jacket for 1–3 hours and followed by discharge into a storage bin or drum (not shown) and held for further processing or packaging.

By way of example, a 3–10 kg of 35% hydrogen peroxide solution has been found effective to sterilize 1000 kg of powder 222. The ratio of hydrogen peroxide to botanical powders may vary and is dependent upon the initial microbial load of the botanical powder 222.

Figure 4:
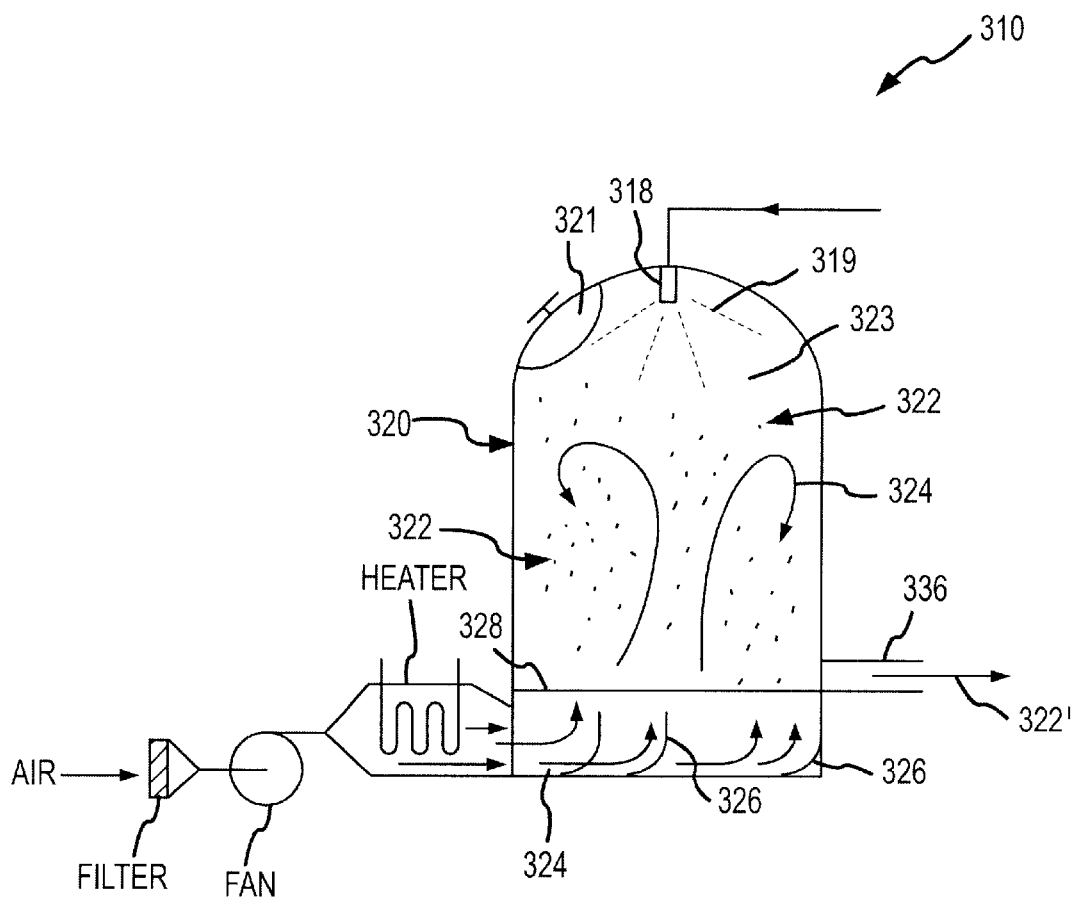
FIG. 4 is a schematic diagram illustrating the HBS process of this invention as applied to a fluid bed system.

In an alternative embodiment the HBS process 310 according to the present invention takes place within a fluid bed 320, as shown in FIG. 4. Fluid bed 320 is constructed so that contaminated botanical powder 322 is first loaded into fluid bed chamber 323 through hatch 321. Heated air 324 is then introduced into fluid bed chamber 323 at a temperature in the range of 30° C.–100° C. and preferably about 60–80° C. Heated air 324 is directed through an air permeable membrane 328 into the interior of fluid bed 320 by directional vanes 326. Air permeable membrane 328 has a pore size that is large enough to allow air to readily pass through but small enough to keep the botanical powder 322 contained within fluid bed chamber 323. Once the botanical powder 322 is mixing within fluid bed chamber 323, a source of nascent oxygen is introduced into fluid bed chamber 323 by way of nozzle 318. As discussed previously, a source of nascent oxygen 319, such as but not limited to hydrogen peroxide, is directed through nozzles 318 thus allowing the source of nascent oxygen 319 to come in contact with the heated botanical powder 322. As the mixing continues the source of nascent oxygen 319 is mixed with the botanical powder and as the source of nascent oxygen 319 comes in contact with the heated air 323 the heat results in the release of nascent oxygen. As the nascent oxygen is released it oxidizes and destroys the existing contaminating microorganisms that it comes into contact with. Mixing continues for a period of 5 minutes to 60 minutes depending upon the volume of botanical powder 322. In the batch-feed operation as illustrated in FIG. 4, an outfeed door 336 is closed until the botanical powder 322 is thoroughly mixed and the decontamination and sterilization has been completed.

At the completion of the mixing sequence, the sterilized botanical powder 322' is discharged into a storage bin (not shown) and held for further processing or packaging. While a batch process has been described in FIG. 4, the equipment could easily be adapted for a continuous process.

By way of example, a 3–10 kg of 35% hydrogen peroxide solution has been found effective to sterilize 1000 kg of botanical powder 322. The ratio may vary and is dependent upon the microbial level of loaded botanical powder 322.

The invention is further illustrated by the following non-limited examples. All scientific and technical terms have the meanings as understood by one with ordinary skill in the art. The specific examples which follow illustrate the methods in which the methodology of the present invention may be preformed and are not to be construed as limiting the invention in sphere or scope. The methods may be adapted to variation in order to produce compositions embraced by this invention but not specifically disclosed. Further, variations of the methods to produce the same compositions in somewhat different fashion will be evident to one skilled in the art.

EXAMPLES

Material and Procedure

Test for Microorganism

Total Aerobic Count (TAC) and Yeast & Mold (Y&M) Count were tested by using the BioMerieux Bactometer method. One gram of sample was added to 99 mL of phosphate dilution buffer (pH 7.2±0.2) (for 1000 cfu/g cutoff), or 10 gram of sample was added to 90 mL of phosphate dilution buffer (for 100 cfu/g cutoff). The mixture was shaken to mix well and a pipette was used to transfer 0.1 mL of this dilution into duplicated wells of a prepared General Purpose Media Bactometer module (for TPC) and a prepared Yeast and Mold Media Bactometer module (for Y&M). The TPC module was incubated in a 35° C. bactometer chamber for 24 hours and the Y&M module was incubated in a 25° C. bactometer chamber for 48 hours. The growth of the microorganism was monitored by the Bactometer Processing System. Based on the results of Bactometer screening, TPC and Y&M counts were confirmed following the procedures published in USP 24. Ten grams of samples were used for analysis. Phosphate dilution buffer or Triptic Soy Broth (TSB) was used for dilution of the samples to expected concentration for yielding 30 to 300 colonies using 1 or 2.5 mL of dilution for each plate. Tryptic Soy Agar (TSA) was used for TPC incubation at 35+2° C. and Sabouraud Dextrose Agar (SDA) was used for Y&M incubation at 25+2° C. The colonies were counted after 48 hours (for TPC) or 5–7 days (for Y&M) using a Spencer Darkfield Colony Counter.

Presence or absence of Salmonella and *Escherichia coli* was tested following the procedures published in USP 24. Enterobacerial Count was tested following the procedures published by Pharmacopeial Forum (Vol. 25(2), page 7761).

Test for Residual Hydrogen Peroxide

Residual hydrogen peroxide was tested using EM Quant® Peroxide Test kits (EM Science, Gibbstown, N.J.). 0.5–1 g of powder was added into 2–4 mL of distilled water (or ethanol or acetone, in the case of organic solvent). The solution was then mixed and sonicated for 5 minutes at room temperature. After sonication, the solution was filtered through a 0.45 $\mu$filter for further use. Dip the test strip into the solution for 1 second. Remove the test strip, shake off excess liquid and compare the reaction zone with color scale after 15 seconds. In the case of organic solvents, dip the test strip into the solution for 1 second. Move the test strip slightly to and fro for 3–30 seconds until the solvent has evaporated from the reaction zone. The rest of the procedure is the same as in the water solution.

Test for Active Components and Chemical Profiles

The active components were tested using high performance liquid chromatography (HPLC) technique and ran on the Hewlett Packard model 1100 equipped with an autosampler, UV/VIS detector, and Hewlett Packard ChemStation software. HPLC conditions included the use of a Phenomenex, Prodigy ODS (5 $\mu$m, 4 IDx125 mm) column or equivalent C-18 column. Gel permeation chromatography (GPC) was performed on PL aquagel-OH 30, (8 $\mu$m, 7.8 IDx30). The proton nuclear magnetic resonance (NMR) spectra were acquired on Unity Inova 400 system, Varian.

Example 1

KH-14-31, 1000 kg of Siberian ginseng (*Eleutherococcus senticosus*) powder (Lot no. 01I-2599) was charged into a modified ribbon blender. 100 kg of 35% hydrogen peroxide solution was sprayed through nozzles within 2 minutes during the blending. After dispersion of the hydrogen peroxide (HP) solution, the mixing powder was then heated for 30 minutes at 50–60° C. A sample (KH-14-31) was taken for microbial test. The untreated material showed a total aerobic count more than 80,000 cfu/g (generally from 10,000 to 100,000 cfu/g), yeast and mold more than 20,000 cfu/g and positive on *E. coli* and Salmonella. After treatment, this sample showed that the total aerobic count is reduced to less than 1000 cfu/g, *E. coli* and Salmonella were non-detectable as well as yeast and mold were less than 100 cfu/g as illustrated in Table 1.

TABLE 1

| Lot No. | Description | TAC* | E&S** | Y&M*** |
|---|---|---|---|---|
| Siberian ginseng | Powder untreated | >80,000 | Positive | >20,000 |
| KH-14-31 | Powder treated | <1000 | Negative | <100 |

*Total aerobic count
**E. coli and Salmonella.
***Yeast and Mold.

Example 2

KH-14-23, 600–700 gallons of water were added into a mixing tank followed by 1000 kg of Siberian ginseng powders (Lot No. 01I-2599) under the agitation for 10 minutes. 100 kg of 35% hydrogen peroxide solution were added slowly and the mixture was stirred for 15 minutes with heating at 50–60° C. This mixture was then pumped to a spray dryer to produce dry powders at 400° F. inlet and 200° F. outlet temperature. The untreated material showed a TAC around 50,000 cfu/g, positive on *E. coli* and Salmonella, as well as yeast and mold more than 1000 cfu/g. After the treatment, the TAC of this powder was reduced to less than 1000 cfu/g, yeast and mold were reduced to less than 100 cfu/g and *E. coli* and Salmonella were completely eliminated to non-detectable as shown in Table 2.

TABLE 2

| Lot No. | Description | TAC | E&S | Y&M |
|---|---|---|---|---|
| Siberian ginseng | Powder untreated | >80,000 | Positive | >20,000 |
| KH-14-23 | Powder treated | <1000 | Negative | <100 |

Comparing before and after treatment, it was observed that the physical properties of the powder that obtained from HBS process were very similar, indicating that such sterilization process will maintain the original properties of powder as showed in Table 3.

TABLE 3

| | | | | | Mass distribution (%)[4] | | |
|---|---|---|---|---|---|---|---|
| Lot No. | Description | LOD[1] (%) | BDL[2] (g/ml) | BDP[3] (g/ml) | Thru 40 | Thru 80 | Thru 200 |
| Siberian ginseng | Powder untreated | 5.84 | 0.31 | 0.54 | 99.8 | 94.0 | 41.8 |
| KH-14-31 | Powder treated | 7.12 | 0.32 | 0.52 | 95.2 | 91.2 | 36.8 |
| KH-14-27 | Powder treated | 5.27 | 0.31 | 0.40 | 100 | 95.0 | 32.9 |

[1]Loss on dry
[2]Bulk density (loose)
[3]Bulk density (pack)
[4]United States Pharmacopoeia SP method, using 40, 80, and 200-mesh screen.

Figure 5:
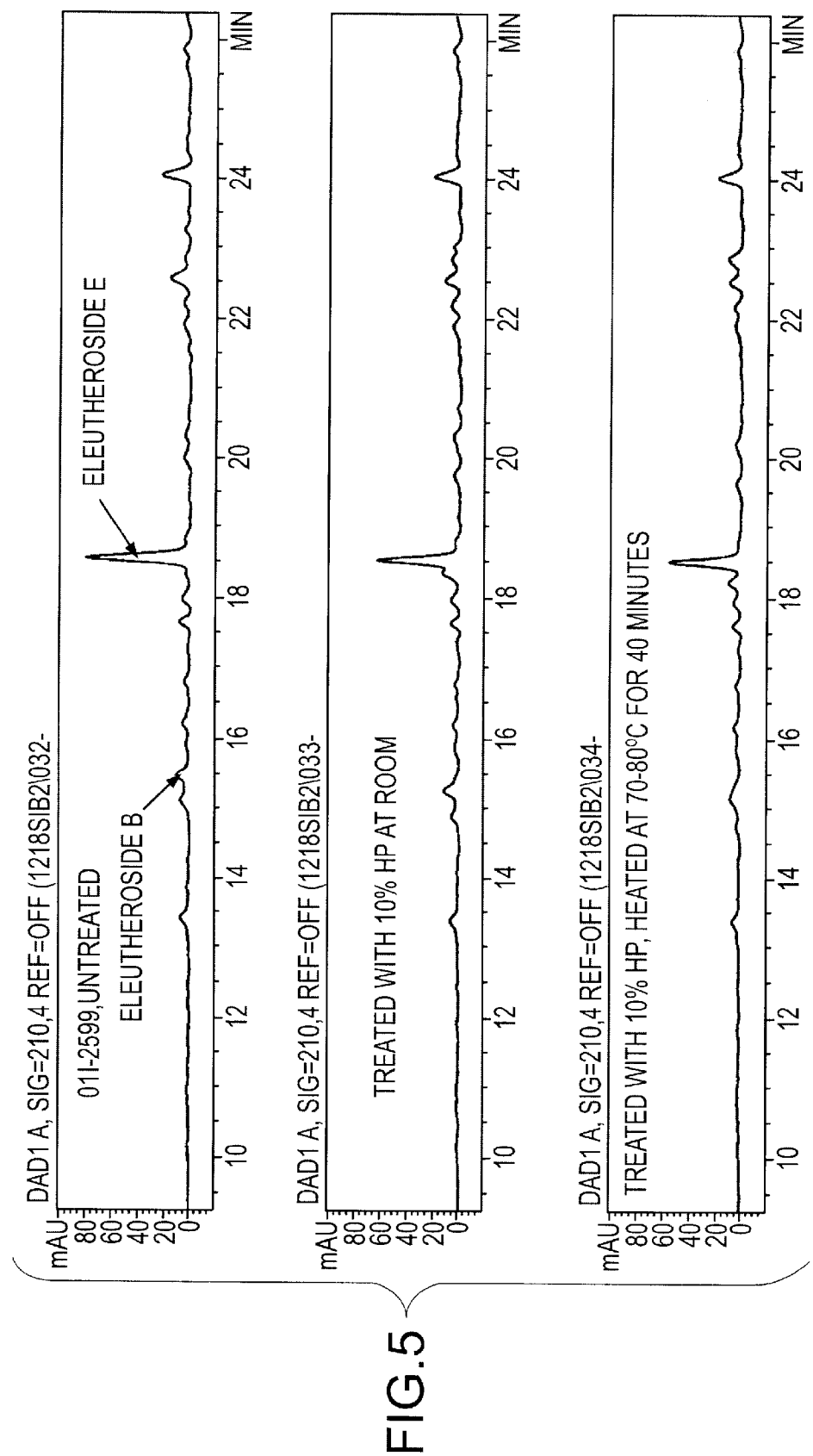
FIG. 5 is an HPLC chromatogram demonstrating that the chemical compositions of a treated Siberian ginseng powder before and after processing have been maintained without significant changed through the sterilization process of the present invention.

Eleutheroside B and E are used as marks in the standardized Siberian ginseng product on the marketplace. It was observed that the contents of eleutheroside B and E, analyzed by high performance liquid chromatography (HPLC), in Siberian ginseng powder (01I-2599) before and after processing, are similar and the chromatogram profile are identical, indicating that the chemical compositions have not been significantly changed through this sterilization process. The HPLC chromatogram is presented in FIG. 5.

Example 3

KH-14-37, 1000 kg of *Echinacea purpurea* powder (Lot no. 01K-3342) was placed into a ribbon blender. A 100 kg of 35% hydrogen peroxide solution was sprayed through nozzles within 2 minutes during the blending. After blending for 30 minutes at 50–60° C., a sample was taken for microbial analysis. The untreated material showed a TAC more than 100,000 cfu/g, positive on *E. coli* and Salmonella, as well as yeast and mold more than 20,000 cfu/g. After the treatment, the TAC of this powder was reduced to less than 1000 cfu/g, yeast and mold were reduced to less than 1000 cfu/g and *E. coli* and Salmonella were completely eliminated to non-detectable shown in Table 4.

TABLE 4

| Lot No. | Description | TAC | E&S | Y&M |
|---|---|---|---|---|
| Echinacea | Raw material | >100,000 | Positive | >20,000 |
| 01K-3400 | Powder treated | <1000 | Negative | <100 |

Figure 6:
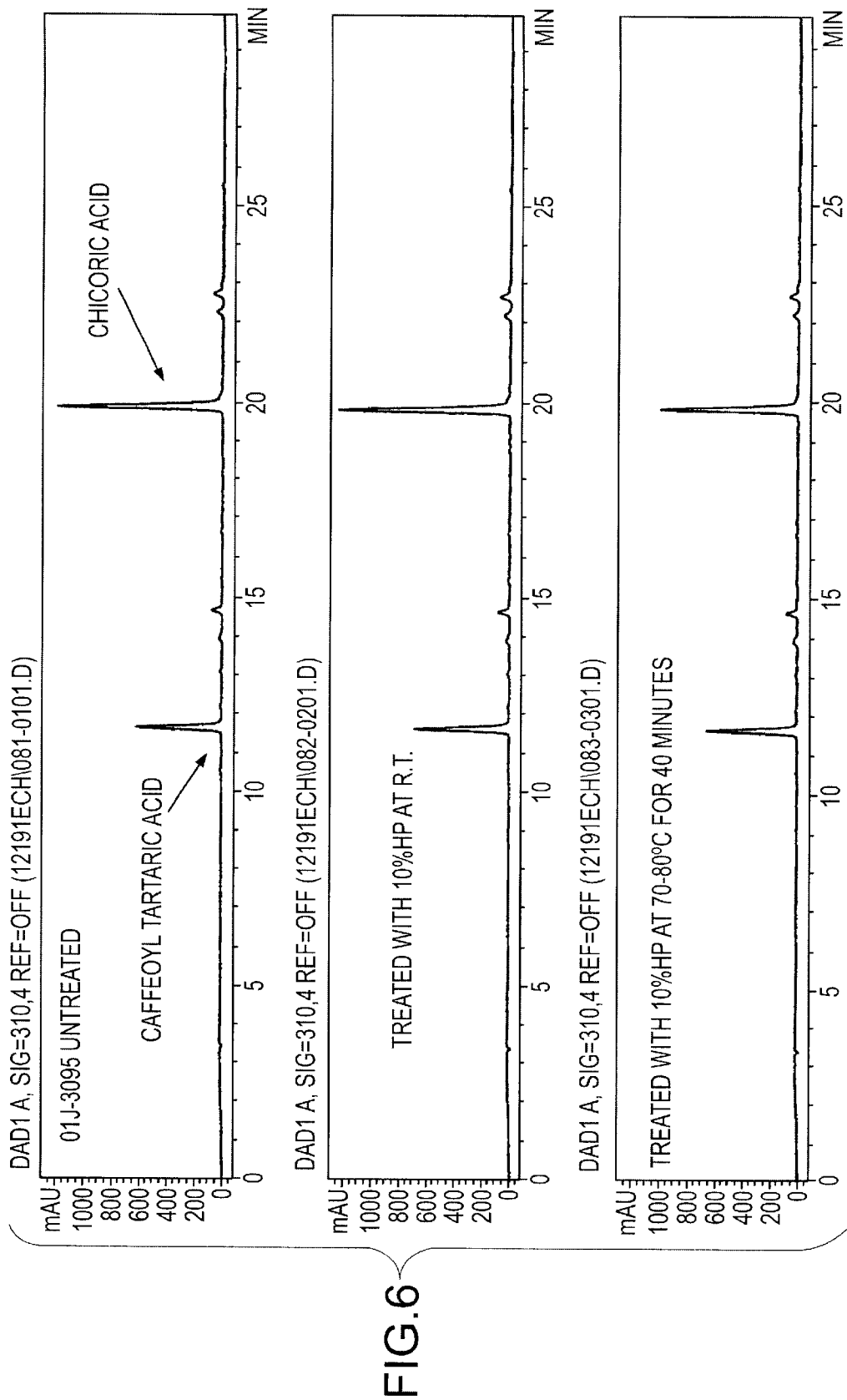
FIG. 6 is an HPLC chromatogram demonstrating that the chemical compositions of a treated *Echinacea purpera* powder before and after processing, have been maintained without significant change through the sterilization process of the present invention.

Chicoric acid and caffeoyal tartaric acid are two major components used as marks in the standardized *Echinacea purpurea* product on the marketplace. In powder of Echinacea (01J-3095), the contents of chicoric acid and caffeoyal tartaric acid, before and after processing, are similar and the chromatogram profile are identical, indicating that the chemical compositions have not been significantly changed through this sterilization process. The HPLC chromatogram is presented in FIG. 6.

Example 4

01K-3558, 1050 kg of Guarana (*Paullinia cupana*) powder (Lot no. 01K-3541) was placed into a ribbon blender. A 106 kg of 35% hydrogen peroxide solution was sprayed through nozzles within 2 minutes during the blending. After blending for 30 minutes at 70–75° C., a sample was taken for microbial analysis. The untreated material showed a TAC more than 20,000 cfu/g, positive on *E. coli* and Salmonella, as well as yeast and mold more than 20,000 cfu/g. After the treatment, the TAC of this powder was reduced to less than 1000 cfu/g, yeast and mold were reduced to less than 1000 cfu/g and *E. coli* and Salmonella were completely eliminated to non-detectable as shown in Table 5.

TABLE 5

| Lot No. | Description | TAC | E&S | Y&M |
|---|---|---|---|---|
| Guarana | Powder untreated | >20,000 | Positive | >20,000 |
| 01K-3558 | Powder treated | <1000 | Negative | <100 |

Figure 7:
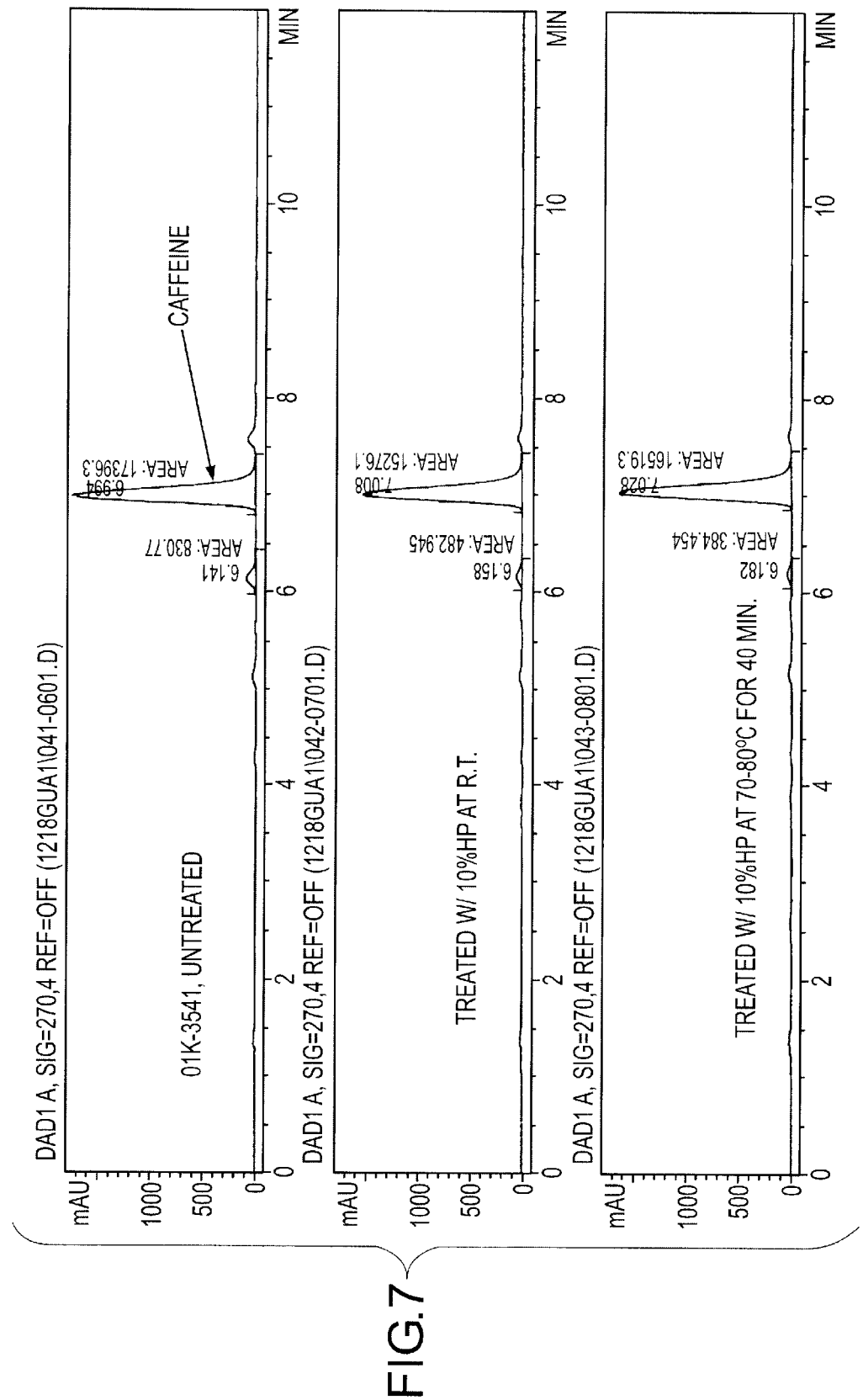
FIG. 7 is a HPLC chromatogram demonstrating that the chemical compositions of an treated Guarana seeds powder before and after processing, have not been significantly changed through the sterilization process of the present invention.

Caffeine is a major component used as mark in the standardized Guarana product on the marketplace. In guarana powder (01K-3541), the content of caffeine, before and after processing, is similar and the chromatogram profiles are identical, indicating that the chemical compositions have not been significantly changed through this sterilization process. The HPLC chromatogram is presented in FIG. 7.

Example 5

01I-3596, 1050 kg of Alfalfa (*Medicago sativa*) powder (Lot No. 01L-3557) was placed into a ribbon blender. A 106 kg of 35% hydrogen peroxide solution was sprayed through nozzles within 2 minutes during the blending. After blending for 30 minutes at 70–75° C., a sample was taken for the microbial test. The untreated material showed a TAC more than 30,000 cfu/g, positive on *E. coli* and Salmonella, as well as yeast and mold more than 20,000 cfu/g. After the treatment, the TAC of this powder was reduced to less than 1,000 cfu/g, yeast and mold were reduced to less than 100 cfu/g and *E. coli* and Salmonella were completely eliminated to non-detectable as shown in Table 6.

TABLE 6

| Lot No. | Description | TAC | E&S | Y&M |
|---|---|---|---|---|
| Alfalfa | Powder untreated | >30,000 | Positive | >20,000 |
| 01I-3596 | Powder treated | <100 | Negative | <100 |

Example 6

01L-3589, 1050 kg of *Cascara sagrada* powder (Lot no. 01K-3530) was placed into a blender. A 105 kg of 35% hydrogen peroxide solution was sprayed through nozzles within 2 minutes during the blending. After blending for 30 minutes at 70–75° C., a sample was taken for the microbial analysis. The untreated material showed a TAC more than 50,000 cfu/g, positive on *E. coli* and Salmonella, as well as yeast and mold more than 20,000 cfu/g. After the treatment, the TAC of this powder was reduced to less than 1000 cfu/g, yeast and mold were reduced to less than 1000 cfu/g and *E. coli* and Salmonella were completely eliminated to non-detectable as shown in Table 7.

TABLE 7

| Lot No. | Description | TAC | E&S | Y&M |
|---|---|---|---|---|
| Cascara | Powder untreated | >50,000 | Positive | >20,000 |
| 01L-3589 | Powder treated | <1000 | Negative | 1000 |

Example 7

ZG2-140-3, 100 g of Ginger (*Zingiber officinalis*) powder (Lot no. 9-3485) was placed into a blender. 10 g of 35% hydrogen peroxide solution was sprayed through nozzles within 2 minutes during the blending. After blending for 30 minutes at 70–75° C., a sample was taken for the microbial analysis. The untreated material showed a TAC more than 26,000 cfu/g. After the treatment, the TAC of this powder was reduced to less than 1000 cfu/g as shown in Table 8.

TABLE 8

| Lot No. | Description | TAC |
|---|---|---|
| Ginger | Powder untreated | >26,000 |
| ZG2-140-3 | Powder treated | <1000 |

Example 8

100 g of Ginkgo (*Ginkgo biloba*) leaf powder (Lot no. 01F-3578) was placed into a blender. 5 g (ZG2-143-3) and 10 g (ZG2-143-4) of 35% hydrogen peroxide solution were sprayed through nozzles within 2 minutes, respectively, during the blending. After blending for 30 minutes at 70–75° C., a sample was taken for the microbial analysis. The untreated material showed a TAC more than 20,000 cfu/g. After the treatment, the TAC of this powder was reduced to less than 1000 cfu/g as shown in Table 9. Low concentration of hydrogen peroxide (5 g of $H_2O_2$ in 100 g powder) also can effectively reduce the microorganism count.

TABLE 9

| Lot No. | Description | TAC* |
|---|---|---|
| Ginkgo Leaf | Powder untreated | >20,000 |
| ZG2-143-3 | Powder treated | <1000 |
| ZG2-143-4 | Powder treated | <1000 |

Example 9

Two 50 g of Siberian ginseng powder (Lot no. 01I-2599) were placed in two blenders and sprayed with 1.5 g of hydrogen peroxide (35% solution). These samples were blended in a blender for 10 minutes. After above treatment, one sample (ZG2-156A1) was stood at room temperature (r.t.) and the other sample (ZG2-156A2) was heated at 70–80° C. for 40 minutes. Sample (ZG2-156A1) showed the TAC more than 1000 cfu/g and sample (ZG2-156A2) showed a TAC less than 1000 cfu/g.

Same procedure were applied to sample (ZG2-156B1) and sample (ZG2-156B2) excepted they were sprayed with 2.5 g hydrogen peroxide (35% solution). Sample ZG2-156B1 showed a TAC more than 1000 cfu/g at room temperature process. Sample ZG2-156B2 showed a TAC less than 1000 cfu/g when heat was applied.

Same procedure were applied to sample (ZG2-156C1) and sample (ZG2-156C2) excepted they were sprayed with 3.5 g hydrogen peroxide (35% solution). Samples ZG2-156C1 and ZG2-156C2 showed a TAC less than 1000 cfu/g when at room temperature or heat was applied. The results and conditions of the experiments are illustrated in the Table 10.

TABLE 10

| Lot No. | 01I-2559 | ZG2-156A1 | ZG2-156A2 | ZG2-156B1 | ZG2-156B2 | ZG2-156C1 | ZG2-156C2 |
|---|---|---|---|---|---|---|---|
| Siberian Ginseng TAC | Untreated | 3%, r.t. | 3%, heated | 5%, r.t. | 5%, heated | 7%, r.t. | 7%, heated |
| | >80,000 | >1000 | <1000 | >1000 | <1000 | >1000 | <1000 |

The above results indicated that even at lower concentration of hydrogen peroxide with elevated temperature it could still effectively reduce the amount of microorganism. No significant changes on both eleutheroside B and E were observed in high concentration of hydrogen peroxide and high temperature.

Example 10

Five 50 g of *Echinacea purpurea* powder (Lot no. 01I-3726) were placed into five blenders and sprayed with different amount of 35% hydrogen peroxide solution, 0.5 g, 1.0 g, 1.5 g, 2.0 g, and 2.5 g, respectively. After that, the five samples were heated at 90–100° C. for 15 minutes to observe the effect of hydrogen peroxide on chemical profiles. No significant changes were observed in the contents of chicoric acid and caffeoyal tartaric acid in the powder before and after processing.

Example 11

Two 100 g of Siberian ginseng powders (Lot No. 01I-2599) were sprayed with 10 g of 32% peracetic acid ($CH_3CO_3H$) in dilute acetic acid solution, respectively. After the treatment, one sample was stood at room temperature (ZG2-152A1) and another was heated at 70–80° C. for 40 minutes (ZG2-152A2). Both samples show the total plate counts less than 1000 cfu/g after the treatment with peracetic acid as shown in the Table 11.

TABLE 11

| Lot No. | 01I-2599 | ZG2-152A1 | ZG2-152A2 |
|---|---|---|---|
| Siberian ginseng TAC | Untreated >80,000 | Peracetic acid 1000 | Peracetic acid 1000 |

Example 12

Two 50 g of Siberian ginseng powders (Lot No. 01I-2599) were blended with 12 g of 20% sodium percarbonate ($Na_2CO_3 \cdot 1.5H_2O_2$) solution, respectively, for 10 minutes. After the treatment, one sample was stood at room temperature (ZG2-163-1) and another was heated at 85–90° C. for 40 minutes (ZG2-163-2). The microbial test results were listed in Table 12.

TABLE 12

| Lot No. | 01I-2599 | ZG2-152B1 | ZG2-152B2 |
|---|---|---|---|
| Siberian Ginseng | Untreated | Sodium percarbonate r.t. | Sodium percarbonate heated |
| TAC | >80,000 | >21,000 | >10,000 |

Example 13

Five 100 g of Cascara powder were sprayed with different amount of 35% hydrogen peroxide solution, 3 g, 5 g, and 10 g, respectively. Each sample was blended in a blender for 10 minutes. After above treatment, samples ZG2-141-1, ZG2-141-2, and ZG2-141-5 were stood at room temperature, while sample ZG2-146-3 was heated at 70–80° C. for 40 minutes, and sample ZG2-146-4 was radiated under the UV light at wavelength 254 nm for 12 hours. The results of microbial analysis were listed in Table 13. Only ZG2-141-5 which was treated with 10 g of 35% hydrogen peroxide solution showed the TAC less then 1000 cfu/g.

TABLE 13

| Lot No. | 01K-3530 | ZG2-141-2 | ZG2-141-1 | ZG2-141-5 | ZG2-146-3 | ZG2-146-4 |
|---|---|---|---|---|---|---|
| Cascara | Untreated | 3%, r.t. | 5%, r.t. | 10%, r.t. | 5%, heated | 5%, UV |
| TAC | >50,000 | >1000 | >1000 | <1000 | >1000 | >1000 |

Example 14

Four 100 g of Psyllium powder were sprayed with different amount of 35% hydrogen peroxide solution, 5 g, 10 g, 15 g, and 20 g, respectively. Each sample was blended in a blender for 10 minutes at room temperature. After above treatment, the samples were incubated for microbial analysis. The results of microbial analysis and hydrogen peroxide residues were listed in the Table 15. At room temperature, it needs about 15 g (15% to powder weight) could effectively reduce total microorganism counts. After the treatment, the residual hydrogen peroxide dropped to nondetectable (ND).

TABLE 15

| Lot No. | 01K-3423 | ZG2-142-1 | ZG2-142-2 | ZG2-142-3 | ZG2-142-4 |
|---|---|---|---|---|---|
| Psyllium | Untreated | 5% | 10% | 15% | 20% |
| TAC | >4000 | >1000 | ~1000 | <1000 | <1000 |
| HP residues |  | ND | ND | ND |  |

Example 15

Three 10 g of Psyllium powder were sprayed with different amount of 35% hydrogen peroxide solution, 5 g, 7 g, and 7 g, respectively. Each samples was blended in a blender for 10 minutes at room temperature. After above treatment, sample ZG2-154A1 and ZG2-154B2 were heated at 70–80° C. for 40 minutes while sample ZG2-154A2 was stood at room temperature for comparison. The results of microbial analysis showed that sample ZG2-154B2, which was treated with 7 g of hydrogen peroxide (7% to powder weight) and heat, the TAC less than 1000 cfu/g, while all the other samples still displayed the TAC more than 1000. The residual hydrogen peroxide reduced to non-detectable. All the results are listed in Table 16.

TABLE 16

| Lot No. | 01K-3423 | ZG2-154A1 | ZG2-154A2 | ZG2-154B2 |
|---|---|---|---|---|
| Psyllium | Untreated | 5%, heated | 7%, r.t. | 7%, heated |
| TAC | >4000 | >1000 | ~1000 | <1000 |
| HP residues |  | ND | ND | ND |

Example 16

1000 g of Psyllium husk (Lot No. OH2159) was sprayed with 100 g of 35% hydrogen peroxide solution (ZG2-149C). Same procedure applied to 1000 g of Psyllium powder (Lot no. OH2159M, ZG2-149D). Both samples were blended for 10 minutes and then heated at 70–80° C. for 40 minutes, respectively. After above treatment, the samples were subject to microbial analyses and the results were summarized in the Table 17. The untreated material showed a TAC more than 10,000 cfu/g, positive on *E. coli* and Salmonella, as well as yeast and mold more than 1000 cfu/g. After the treatment, the TAC of this powder was reduced to less than 10 cfu/g, yeast and mold were reduced to less than 1000 cfu/g and *E. coli* and Salmonella were completely eliminated to non-detectable shown in Table 17.

TABLE 17

| Lot No. | OH2159 | ZG2-149C | OH2159M | ZG2-149D |
|---|---|---|---|---|
| Psyllium | Untreated | 10% | Untreated | 10% |
| TAC | >10,000 | <1000 | >10,000 | <1000 |
| Yeast & mold | 11,000 | <10 |  | <10 |
| *E. coli* | Positive | Negative | Positive | Negative |
| Salmonella | Positive | Negative | Positive | Negative |
| Enterobacterial |  | Negative |  | Negative |

Figure 8:
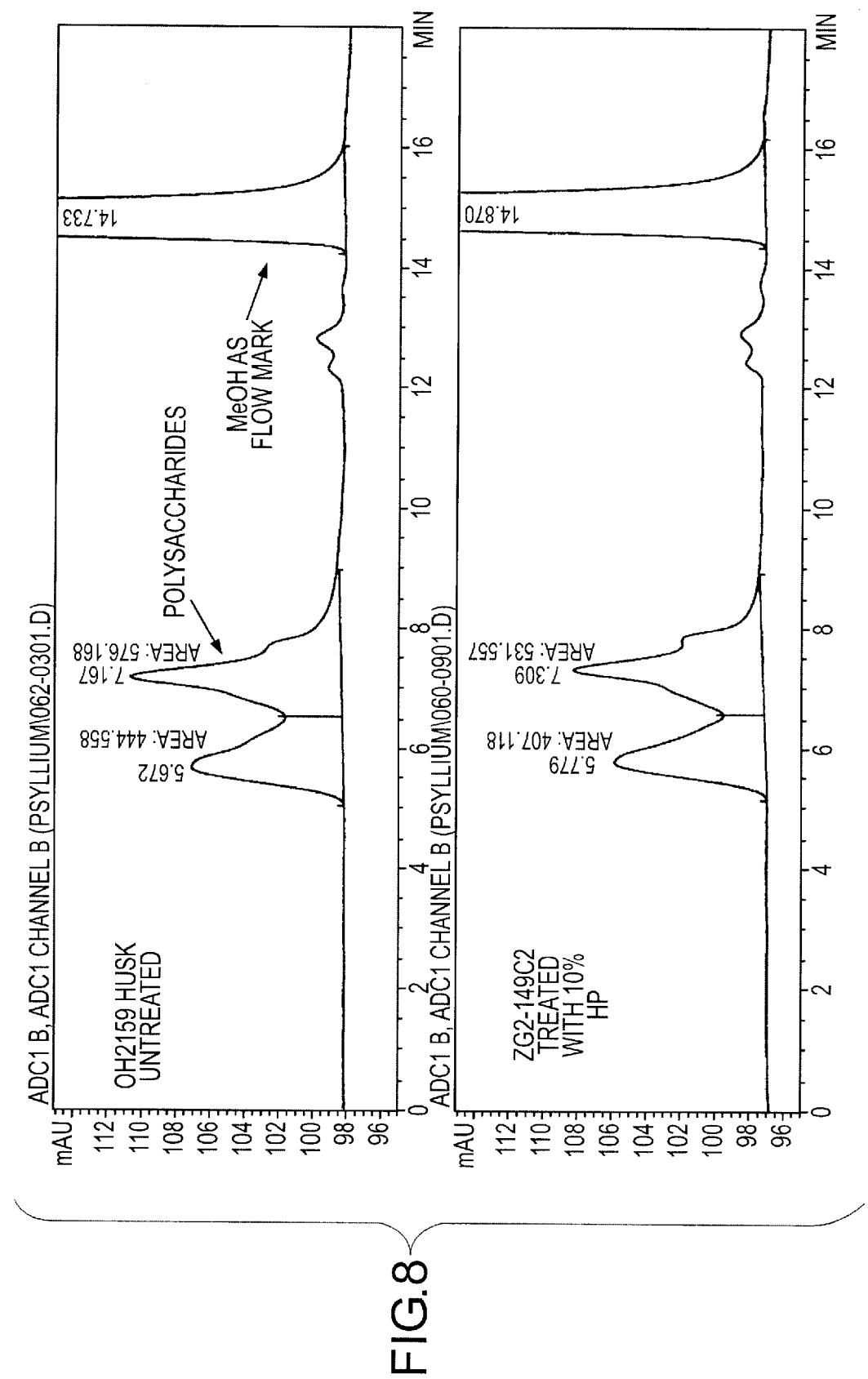
FIG. 8 is a GPC (gel permeation chromatography) chromatogram demonstrating that the chemical compositions of polysaccharides of a treated Psyllium husk before and after processing, have not been significantly changed through the sterilization process of the present invention.
Figure 9:
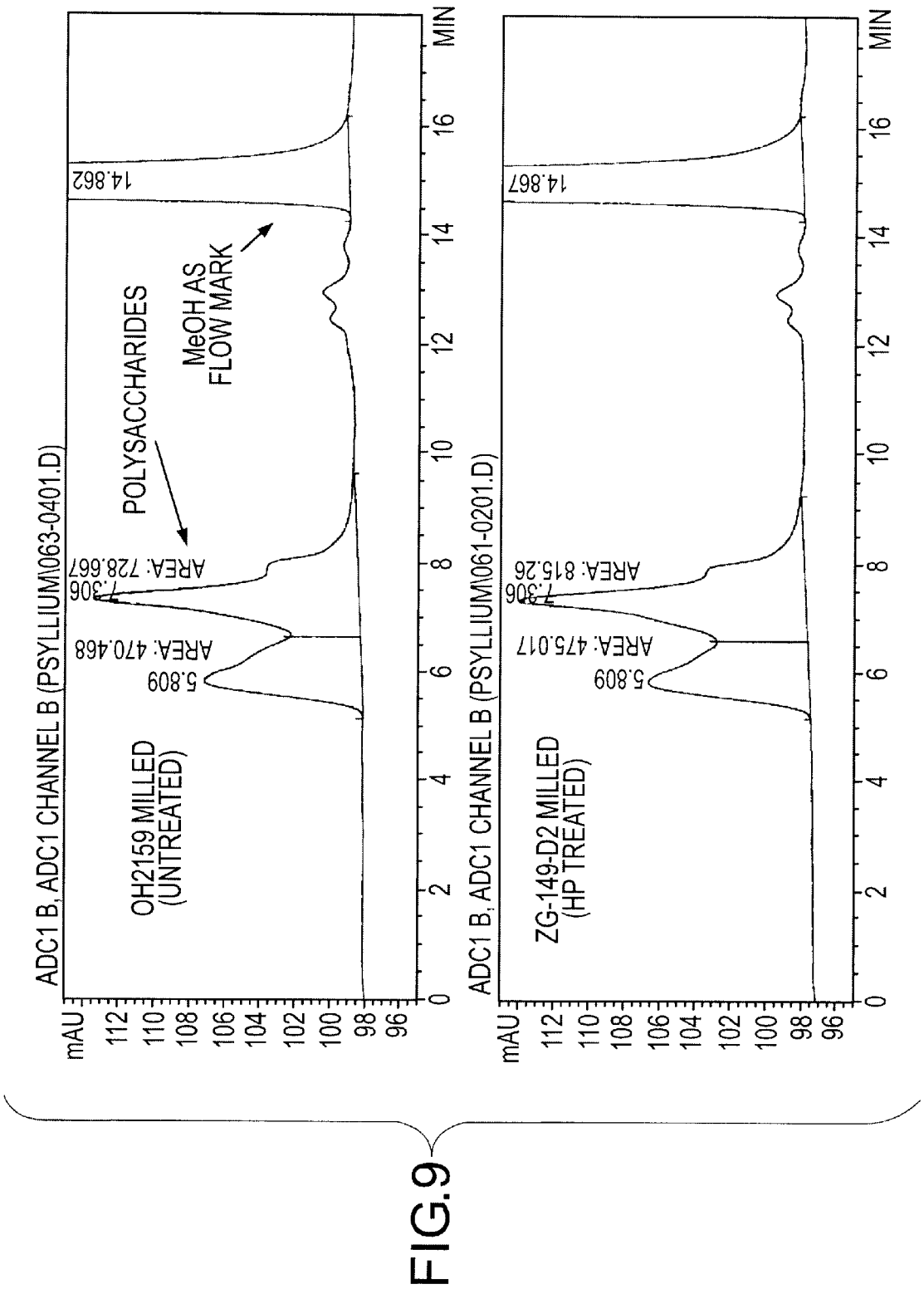
FIG. 9 is a GPC chromatogram demonstrating that the chemical compositions of a treated Psyllium milled powder before and after processing, have not been significantly changed through the sterilization process of the present invention.
Figure 10:
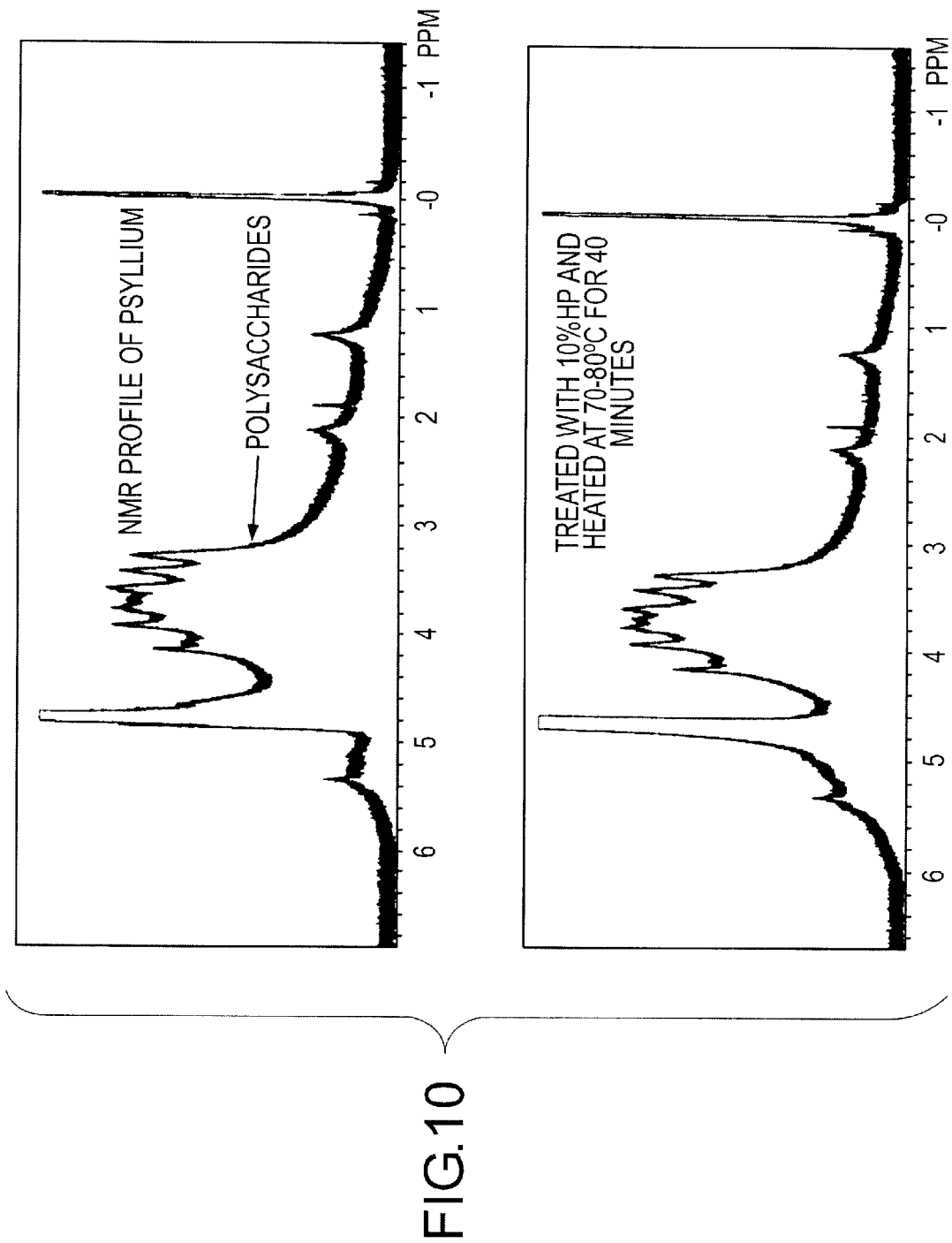
FIG. 10 is an $^1H$ NMR spectra demonstrating that the proton profile of a treated Psyllium before and after processing have not been significantly changed through the sterilization process of the present invention.

The physical and chemical properties of Psyllium were also compared before and after treatment by hydrogen peroxide solution. Since the fiber (polysaccharides) in Psyllium is the active components, the methods which can be used to evaluate the polysaccharide properties were chosen for the comparison. No significant changes were observed on the following experiments before and after treatment. The water absorption value, which was based on United States Pharmacopoeia procedure to evaluate polysaccharide polymer characteristic, was the same. The proton nuclear magnetic resonance (NMR) spectra, which display polysaccharide signals, were similar. The retention time and chromatograms, as well as peak area on the gel permeation chromatography (GPC), which were used to evaluate polysaccharide size and quantities, were similar before and after treatment. All these results indicate that the active components, polysaccharides, in Psyllium have not changed after the treatment of hydrogen peroxide solution. The GPC chromatograms and $^1$H NMR spectra are presented in FIGS. 8–10.

Example 17

Two 50 g of Psyllium husk were sprayed with 2.5 g of 50% hydrogen peroxide solution, respectively. Each sample was blended for 10 minutes. One sample (ZG2-158-1) was kept at room temperature and another (ZG2-158-2) was heated at 70–80° C. for 40 minutes. After the above treatment, the samples were subject to microbial analyses and the result is listed in the following table. The non-heated sample showed the TAC assay at the beginning was more than 1000 cfu/g and less than 1000 cfu/g after the sample settled at room temperature for another day, which indicated that the effect of disinfection of hydrogen peroxide requires a certain amount of time under no heat conditions. Residual hydrogen peroxide was below 0.5 ppm after days. These data are listed in Table 18.

TABLE 18

| Lot No. | 01K-3423 | ZG2-158-1 | ZG2-158-1 | ZG2-158-2 |
|---|---|---|---|---|
| Psyllium | Untreated | 5% (50% HP), r.t. | 5% (50% HP), r.t. | 5% (50% HP), heated |
| TAC | >4000 | >1000 | <1000 | <1000 |

Example 18

*Echinacea purpurea* powder was treated with different concentration of hydrogen peroxide solution, 1%, 2%, 3%, 4%, and 5% of 35% hydrogen peroxide solution, and then heated at 90–100° C. for 15 minutes. After above treatment, the samples were subject to microbial analyses and the result are listed in Table 19.

TABLE 19

| Lot No. | 01L-3726 | ZG2-157-1 | ZG2-157-2 | ZG2-157-3 | ZG2-157-4 | ZG2-157-5 |
|---|---|---|---|---|---|---|
| Echinacea | Untreated | 1% | 2% | 3% | 4% | 5% |
| TAC | >100,000 | >1000 | >1000 | >1000 | >1000 | >1000 |

Example 19

300 kg of Psyllium husk was placed into a ribbon blender. A 15 kg of 35% hydrogen peroxide solution was sprayed through nozzles within 2 minutes during the blending. After blending for 30 minutes at 70–75° C., a sample was taken and tested for the microbial analysis. After the sample was taken, another 15 kg of 35% hydrogen peroxide was sprayed through nozzles within 2 minutes during the blending. After blending for 30 minutes at 70–75° C., the second sample was taken and tested for the microbial analysis. Microbial testing results were listed in the Table 20. The final product which was treated with 30 kg (9% to powder weight) of 35% hydrogen peroxide solution showed the TAC less than 1000 cfu/g, yeast and mold less than 100 cfu/g and *E. coli* and Salmonella non-detectable.

TABLE 20

| Lot No. | 02A-0001-0 | 02A-0001-1 | 02A-0001-2 |
|---|---|---|---|
| Psyllium | Untreated | 5% HP | 10% HP |
| TAC | >10,000 | >1000 | <1000 |
| HP residues | | N.A. | Non detectable |

Example 20

10 g of Siberian ginseng powder (Lot No. 01I-2599) was placed into a beaker and sprayed with 1.5 g of hydrogen peroxide (35% solution). 40 g of water was added into the beaker and mixed for 30 minutes at room temperature. After 24 hours, the sample was subjected to microbial testing and it showed the TAC more than 1000 cfu/g.

Example 21

10 g of Siberian ginseng powder (Lot No. 01I-2599) was placed into a beaker and sprayed with 3 g of hydrogen peroxide (35% solution). 40 g of water was added into the beaker and mixed for 30 minutes at room temperature. After 24 hours, the sample was subjected to microbial testing and it showed the TAC less than 1000 cfu/g.

Example 22

10 g of Siberian ginseng powder (Lot No. 01I-2599) was placed into a beaker and sprayed with 3 g of hydrogen peroxide (35% solution). 40 g of water was added into the beaker and mixed for 30 minutes at room temperature. The samples were subjected to microbial testing after 15 and 60 minutes respectively. Both samples showed the TAC more than 1000 cfu/g.

Example 23

10 g of Siberian ginseng powder (Lot No. 01I-2599) was placed into a beaker. 56 g of water was added into the beaker and heated at 90° C. Samples were taken after 1, 2, and 3 hours, respectively. These samples were subjected to microbial testing and two samples which were heated for 1 and 2 hours showed TAC more than 1000 cfu/g. The sample which was heated for 3 hours showed the TAC less than 1000 cfu/g, but more than 1000 cfu/g after the sample was settled at room temperature for 4 days.

Example 24

95 g of Siberian ginseng powder (Lot No. 01I-2599) was placed into a beaker and sprayed with 5 g of hydrogen peroxide (35% solution). The sample was heated in an oven at 50–55° C. for 0.5 hour. The sample was subjected to microbial testing and it showed the TAC more than 1000 cfu/g.

Example 25

90 g of Siberian ginseng powder (Lot No. 01I-2599) was placed into a beaker and sprayed with 10 g of hydrogen peroxide (35% solution). The sample was heated in an oven at 50–55° C. for 0.5 hour. The sample was subjected to microbial testing and it showed the TAC less than 1000 cfu/g.

Example 26

100 kg of Siberian ginseng powder (Lot No. 01I-2599) was placed into a 500 gallon mixing tank and sprayed with 25 kg of hydrogen peroxide (35% solution). Add 130 gallons of water and mix for 30 minutes. Before spray drying, a sample was picked for microbial testing and it showed the TAC of more than 1000 cfu/g but less than 5000. After spray drying at inlet temperature 450° F., the dried powder was tested and showed the TAC less than 1000 cfu/g.

Example 27

100 kg of Siberian ginseng powder (Lot No. 01I-2599) was placed into a 500-gallon mixing tank and 130 gallons of water was added. The mixed material was heated at 80–90° C. for 0.5 hour and then was spray dried. After spray drying at inlet temperature of 450° F., the dried powder was tested and it showed the TAC more than 1000 cfu/g.

Example 28

1000 kg of Psyllium husk (Lot No. 02A-0045) was placed into a ribbon blender. Blended at 70–80° C. for 10 minutes. A 50 kg of 35% hydrogen peroxide solution was sprayed through nozzles within 2 minutes during the blending. After blending for 30 minutes at 70–80° C., a sample was taken and tested for the microbial analysis. After the sample was taken, another 50 kg of 35% hydrogen peroxide was sprayed through nozzles within 2 minutes during the blending. After blending for 30 minutes at 70–80° C., the second a sample was taken and tested for the microbial analysis. Microbial testing results were listed in the Table 21. The final product which was treated with 100 kg (9% to powder weight) of 35% hydrogen peroxide solution showed the TAC less than 100 cfu/g, yeast and mold less than 100 cfu/g and E. coli and Salmonella non-detectable as shown in Table 21.

TABLE 21

| Lot No. | 02A-0045-0 | 02A-0045-1 | 02A-0045-2 |
|---|---|---|---|
| Psyllium | Untreated | 50 kg HP | 100 kg HP |
| TAC | 36,000 | 2000 | 80 |
| E&S | Positive | Negative | Negative |
| Y&M | 14,000 | <200 | <200 |
| Residual HP | | | Non detectable |

Example 29

50 g of Psyllium husk were placed into a blender followed by spraying 3.5 g of hydrogen peroxide solution (35%) through a nozzle during the blending. There was hydrogen peroxide residue remaining in the product. After complete addition of hydrogen peroxide, 0.5 g of vitamin C powder was added and blended in the blender for an additional 1 minute. No residual hydrogen peroxide was detected after the psyllium was kept at room temperature for 2 to 24 hours.

Example 30

50 g of Psyllium husk were placed into a blender followed by spraying 3.5 g of hydrogen peroxide solution (35%) through a nozzle during the blending. There was hydrogen peroxide residue remained in the product. After complete addition of hydrogen peroxide, 0.5 g of vitamin C solution (25% vitamin C in water) was sprayed and blended in the blend for additional 5 minute. No residual hydrogen peroxide was detected after the psyllium was stirred at room temperature for 10 minutes.

Example 31

To a 5 foot diameter spray dryer, 20 kg of Psyllium husk were pumped into the drying chamber from top of the dryer at a rate of 20 kg/hr. While psyllium husk was introduced, a hydrogen peroxide solution (3%), which is premixed in batching tank by diluting hydrogen peroxide (35% solution) with water, was sprayed through the atomizer. The inlet temperature was controlled at 350° F. and the outlet temperature was controlled at 200° F. The psyllium husk was contacted with atomic oxygen released from hydrogen peroxide and dried at the same time. The total aerobic count of the psyllium husk was reduced to specification.

The foregoing description is considered as illustrative only of the principles of the invention. The words "comprise," "comprising," "include," "including," and "includes" when used in this specification and in the following claims are intended to specify the presence of one or more stated features, integers, components, or steps, but they do not preclude the presence or addition of one or more other features, integers, components, steps, or groups thereof. Furthermore, since a number of modifications and changes will readily occur to those skilled in the art, it is not desired to limit the invention to the exact construction and process shown described above. Accordingly, all suitable modifications and equivalents may be resorted to falling within the scope of the invention as defined by the claims which follow.

The embodiments of the invention in which an exclusive property or privilege is claimed are defined as follows:

1. A method of sterilizing agricultural products contaminated with microorganisms comprising,
   mixing an agricultural product with a source of nascent atomic oxygen:
   exposing said source of nascent atomic oxygen, at ambient pressure, to an energy source that is sufficient to heat said source of nascent atomic oxygen to a temperature at which the source releases said nascent atomic oxygen, wherein said temperature is between about 200 and about 500° F.; and
   contacting the agricultural product with said nascent atomic oxygen for a period of time sufficient for the contaminating microorganisms to be oxidized.

2. The method of claim 1, wherein said source of nascent oxygen is hydrogen peroxide.

3. The method of claim 1, wherein said source of nascent atomic oxygen is peroxyacetic acid.

4. The method of claim 1, wherein said source of nascent oxygen is sodium percarbonate.

5. The method of claim 1, wherein said agricultural product is a botanical product.

6. The method of claim 5, wherein said botanical product is a powder.

7. The method of claim 5, wherein said agricultural product is in the form of roots, husks, fruits, flowers, barks, leaves, and seeds.

8. The method of claim 1, wherein said agricultural product is spice, gum, dried vegetable.

9. The method of claim 1, further comprising exposing a source of hydroxyl radicals to a sufficient level said energy to release said hydroxyl radicals.

10. A method of sterilizing agricultural products contaminated with microorganisms comprising,
    forming a feed comprising a source of nascent atomic oxygen, water and a botanical powder, wherein the water comprises 10 to 60 percent of the weight of the feed;
    directing said feed into a chamber, at ambient pressure; and
    contacting said feed for a period of time sufficient with a temperature necessary to degrade said source of nascent atomic oxygen to release nascent atomic oxygen.

11. The method of claim 10, wherein said source of nascent atomic oxygen is hydrogen peroxide.

12. The method of claim 10, wherein said source is peroxyacetic acid or sodium percarbonate.

13. The method of claim 10, wherein said source of nascent atomic oxygen is present in a quantity of 1%–10% by weight of said botanical powder.

14. The method of claim 10, wherein said temperature is at a temperature in the range of 100–500° F.

15. The method of claim 10, wherein said directing of feed into said chamber includes atomizing at least a portion of the feed in the chamber prior to the contacting the feed with the degradation temperature.

16. A method of sterilizing botanical powders contaminated with microorganisms comprising, forming a feed comprising hydrogen peroxide, water and a botanical powder, wherein said hydrogen peroxide is present in a quantity of 1 to 10 percent by weight of said botanical powder;

directing said feed into a chamber, at ambient pressure; and contacting said feed for a period of time sufficient with a temperature necessary to degrade said hydrogen peroxide to release nascent atomic oxygen.

17. A method of sterilizing agricultural products contaminated with microorganisms comprising, blending the agricultural product in a vessel;

heating the vessel to maintain an internal sidewall of the vessel above a predetermined degradation temperature:

contacting a source of nascent atomic oxygen with said agricultural product while maintaining continued blending; and degrading said source of nascent atomic oxygen.

18. The method of claim 17, wherein said heated blender is a ribbon blender.

19. The method of claim 17, wherein said agricultural product is a botanical powder.

20. The method of claim 19, wherein said botanical powder is ginseng.

21. The method of claim 19, wherein said botanical powder is cascara.

22. The method of claim 19, wherein said botanical powder is Echinacea.

23. The method of claim 19, wherein said botanical powder is Psyllium.

24. The method of claim 17, wherein said source of nascent atomic oxygen is hydrogen peroxide.

25. The method of claim 17, wherein said source of atomic oxygen is peroxacetic acid or sodium percarbonate.

26. A method of sterilizing agricultural products contaminated with microorganisms comprising, placing said agricultural products in a fluid bed at ambient pressure;

flowing heated air into said fluid bed at a force sufficient to mix said agricultural products;

contacting the contaminated agricultural product with a source of nascent atomic oxygen for a contact period of less than about 60 minutes wherein said heated air causes said source of nascent atomic oxygen to decompose and release said nascent atomic oxygen in quantities sufficient for the contaminating microorganisms to be oxidized.

27. The method of claim 1, wherein the exposing said source of nascent atomic oxygen is performed in a drying chamber and wherein the period of time for contacting is determined by time taken for the agricultural product to drop from an inlet in the drying chamber to about a bottom of the drying chamber.

28. The method of claim 1, wherein the exposing said source of nascent atomic oxygen is performed in a drying chamber, the energy source comprising drying air at a temperature between about 200 and about 500° F. introduced into the drying chamber.

29. The method of claim 17, wherein the degradation temperature is in the range of 40 to 100° C.

* * * * *